(12) United States Patent
Reszka et al.

(10) Patent No.: US 6,416,964 B2
(45) Date of Patent: *Jul. 9, 2002

(54) METHODS OF IDENTIFYING MODULATORS OF KINASES RESPONSIVE TO STRESS

(75) Inventors: Alfred A. Reszka, Glenside; Gideon A. Rodan, Bryn Mawr, both of PA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/238,536

(22) Filed: Jan. 27, 1999

Related U.S. Application Data

(60) Provisional application No. 60/108,306, filed on Nov. 13, 1998, provisional application No. 60/106,287, filed on Oct. 30, 1998, provisional application No. 60/077,582, filed on Mar. 10, 1998, provisional application No. 60/085,452, filed on May 14, 1998, and provisional application No. 60/072,940, filed on Jan. 29, 1998.

(51) Int. Cl.$^7$ .................................................. C12Q 1/48
(52) U.S. Cl. ........................ 435/15; 435/4; 435/194; 435/325; 435/366
(58) Field of Search ........................... 435/4, 194, 15, 435/325, 366

(56) References Cited

U.S. PATENT DOCUMENTS

| | | | |
|---|---|---|---|
| 4,621,077 A | 11/1986 | Rosini et al. | ............... 514/108 |
| 5,830,699 A | 11/1998 | Force et al. | ............... 435/69.1 |

OTHER PUBLICATIONS

Taylor et al., Proc. Nat'l. Acad. Sci. USA, vol. 93, pp. 10099–10104 (1996), "Newly identified stress–responsive protein kinases, Krs–1 and Krs–2".

Creasy et al., J. of Biol. Chem., vol. 270, No. 37, pp. 21695–21700 (1995), "Cloning and characterization of a human protein kinase with homology to Ste20".

Creasy et al., Gene, vol. 167, pp. 303–306 (1995), "Cloning and characterization of a member of the MST subfamily of Ste20–like kinases".

Schmidt et al., Proc. Nat'l. Acad. Sci. USA, vol. 93 (1996), pp. 3068–3072, "Protein–tyrosine phosphatase activity regulates osteoclast formation and function . . . ".

Schinkmann et al., J. of Biol. Chemistry, vol. 272 (1997), pp. 28695–28703, "Cloning and characterization of a human STE20–like protein kinase with unusual cofactor requirements".

Creasy et al., J. of Biol. Chem., vol. 271, No. 35, pp. 21049–21053 (1996), "The Ste20–like protein kinase, Mst1, dimerizes and contains an inhibitory domain".

Wang et al., Mol. Biol. Cell, vol. 3, pp. 1329–1337 (1992), "Activation of protein serine/threonine kinases p42, p63, and p87 in Rous sarcoma virus–transformed cells: signal transduction/transformation–dependent MBP kinases".

Graves et al., The EMBO Journal, vol. 17, No. 8, pp. 2224–2234 (1998), "Caspase–mediated activation and induction of apoptosis by the mammalian Ste2–like kinase Mst1".

Wesolowski et al., Exp. Cell Res., vol. 219, pp. 679–686 (1995), "Isolation and characterization of highly enriched, prefusion mouse osteoclastic cells".

Kameshita et al., Anal. Biochem., vol. 183, pp. 139–143, "A sensitive method for detection of calmodulin–dependent protein kinase II activity in sodium dodecyl sulfate–polyacrylamide gel".

Gotoh et al., Eur. J. Biochem., vol. 193, pp. 661–669, "Microtubule–associated–protein (MAP) kinase activated by nerve growth factor and epidermal growth factor in PC12 cells".

Tewari et al., J. of Biol. Chem., vol. 270, No. 7, pp. 3255–3260 (1995), "Fas– and tumor necrosis factor–induced apoptosis is inhibited by the poxvirus crmA gene product".

Enari et al., Nature, vol. 380, pp. 723–726, "Sequential activation of ICE–like and CPP32–like proteases during Fas–mediated apoptosis".

Enari et al., Nature, vol. 375, pp. 78–81, "Involvement of an ICE–like protease in Fas–mediated apoptosis".

Los et al., Nature, vol. 375, pp. 81–83, "Requirement of an ICE/CED–3 protease for Fas/APO–1–mediated apoptosis".

*Primary Examiner*—Leon B. Lankford, Jr.
(74) *Attorney, Agent, or Firm*—Nicole M. Wallinger; Mark R. Daniel

(57) ABSTRACT

The present invention relates to methods of identifying compounds useful as modulators of certain stress responsive kinases. More particularly, the compounds so identified are useful for treating or preventing diseases or conditions that are mediated by, for example, abnormal bone resorption or angiogenesis. These compounds are useful for treating or preventing osteoporosis, and inhibiting vascular restenosis, diabetic retinopathy, macular degeneration, angiogenesis, atherosclerosis, inflammation, and tumor growth.

4 Claims, 11 Drawing Sheets

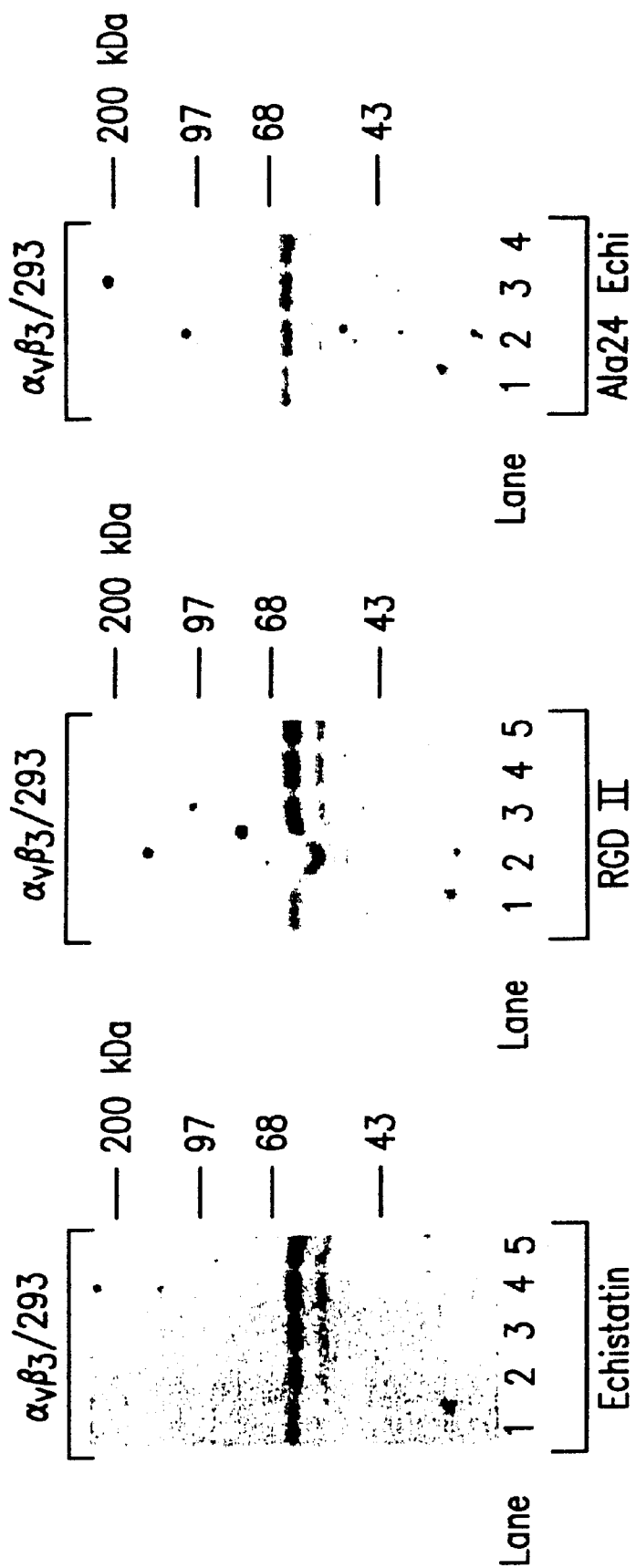

METHODS OF IDENTIFYING MODULATORS OF KINASES RESPONSIVE TO STRESS

CROSS-REFERENCE TO RELATED APPLICATIONS

The present application claims priority of U.S. provisional application Ser. No. 60/108,306, filed Nov. 13, 1998; U.S. provisional application Ser. No. 60/106,287, filed Oct. 30, 1998; U.S. provisional application Ser. No. 60/085,452, filed May 14, 1998; U.S. provisional application Ser. No. 60/077,582, filed Mar. 10, 1998; and U.S. provisional application Ser. No. 60/072,940, filed Jan. 29, 1998.

BRIEF DESCRIPTION OF THE INVENTION

The present invention relates to methods of identifying compounds useful as modulators, particularly activators, of certain stress responsive kinases. More particularly, the compounds so identified are useful for treating or preventing diseases or conditions that are mediated by, for example, abnormal bone resorption or angiogenesis. These compounds are useful for treating or preventing osteoporosis, and inhibiting vascular restenosis, diabetic retinopathy, macular degeneration, angiogenesis, atherosclerosis, inflammation, and tumor growth.

BACKGROUND OF THE INVENTION

It is believed that at least a dozen kinds of kinases responsive to stress exist in various mammalian cells. One of these kinases, the Mammalian Sterile 20-like Kinase has recently been described in the scientific literature. At least two isoforms of Mammalian Sterile 20-like Kinase are known, hereafter referred to as "Mst 1" and "Mst 2". See, Taylor et al., "Newly identified stress-responsive protein kinases, Krs-1 and Krs-2", *Proc. Natl. Acad. Sci. USA*, Vol. 93 (1996), pp. 10099–10104; Creasy et al., "Cloning and characterization of a human protein kinase with homology to Ste20," *The J. of Biological Chemistry*, Vol. 270, No. 37 (1995), pp. 21695–21700; Creasy et al., "Cloning and characterization of a member of the MST subfamily of Ste20-like kinases", *Gene*, Vol. 167 (1995), pp. 303–306; Creasy et al., "The Ste 20-like protein kinase, Mst 1, dimerizes and contains an inhibitory domain", *The J. of Biological Chemistry*, Vol. 271, No. 35 (1996), pp. 21049–21053; and Wang and Erikson, "Activation of protein serine/threonine kinases p42, p63, and p87 in Rous sarcoma virus-transformed cells: signal transduction/transformation-dependent MBP kinases", *Mol. Biol. Cell*, 3, pp. 1329–1337 (1992), which are all incorporated by reference herein in their entirety. As part of the present invention, three other kinases have been identified using an in-gel kinase assay. These kinases have a molecular weight of approximately 34 kDa, 50 kDa, and 130 kDA and will be referred to herein as "34 kDa Kinase", "50 kDa Kinase", and "130 kDa Kinase", respectively. It is believed that Mst 1, Mst 2, 34 kDa Kinase, 50 kDa Kinase and 130 kDa Kinase play a key role in regulating various mammalian cells such as osteoclasts and in regulating cellular processes such as angiogenesis.

It is believed that a wide variety of disease states and conditions can be mediated by modulating, for example by activating, Mst 1, Mst 2, 34 kDa Kinase, 50 kDa Kinase, or 130 kDa Kinase, or combinations thereof. It is also believed that so-called modulators of these kinases represent a new and useful therapeutic class of drugs. Such modulators would be useful for treating or preventing diseases which include osteoporosis, osteopenia, and Paget's disease, and for inhibiting vascular restenosis, diabetic retinopathy, macular degeneration, angiogenesis, atherosclerosis, inflammation, and tumor growth.

In one aspect of the present invention, the activator compounds herein are useful for inhibiting bone resorption. Bone resorption is mediated by the action of cells known as osteoclasts. Osteoclasts are large multinucleated cells of up to about 400 $\mu$m in diameter that resorb mineralized tissue in vertebrates. Osteoclasts are actively motile cells that migrate along the surface of bone, and can bind to bone, secrete necessary acids and proteases, thereby causing the actual resorption of mineralized tissue of the bone. More specifically, osteoclasts are believed to exist in at least two physiological states, i.e. the active/secretory state and the migratory or motile state. In the secretory state, osteoclasts are flat, attach to the bone matrix via a tight attachment, i.e. sealing, zone, become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they again attach to bone. Kinases such as Mst 1, Mst 2, 34 kDa Kinase, 50 kDa Kinase, and 130 kDa Kinase are believed to be involved in the regulation of osteoclast function. Therefore, by targeting these kinases, osteoclast mediated disease states, for example osteoporosis, can be treated.

In the present invention, it was unexpectedly discovered that certain compounds that are known to modify osteoclast function activate stress reponsive kinases. These activating compounds are the bisphosphonate alendronate, the snake venom disintegrin echistatin, anti β3 integrin monoclonal antibody (commercially available from Pharmingen, San Diego, Calif.), the naturally occurring polypeptide calcitonin, and the echistatin RGD (i.e. arginine, glycine, aspartate) mimetics 3(S)-(2-(2-oxo-3(S)-[5,6,7,8-tetrahydro-[1,8]-naphthyridin-2-ylmethyl)-amino]-pyrrolidin-1-yl)-acetylamino)-4-quinolin-3-yl-butyric acid trihydrochloride (hereafter "RGD I") and (2-[N-(3,4,5,6-tetrahydropyrimidin-2-yl)amino]ethyloxyphen-4-yl)carbonyl-2(S)-phenylsulfonamido-beta-alanine (hereafter "RGD II"). This unexpected finding led to the further discovery of providing methods of identifying compounds which activate these kinases and the realization that other compounds so-identified would be useful for treating a variety of conditions or disease states mediated by these kinases.

It is therefore an object of the present invention to provide methods for identifying compounds which modulate a kinase responsive to stress selected from the group consisting of Mst 1, Mst 2, 34 kDa Kinase, 50 kDa Kinase, and 130 kDa Kinase and mixtures thereof.

It is another object of the present invention to provide methods of activating in mammalian cells a kinase responsive to stress selected from the group consisting of Mst 1, Mst 2, 34 kDa Kinase, 50 kDa Kinase, and 130 kDa Kinase and mixtures thereof.

It is another object of the present invention to provide methods of eliciting an activating effect in a mammal of a kinase responsive to stress selected from the group consisting of Mst 1, Mst 2, 34 kDa Kinase, 50 kDa Kinase, and 130 kDa Kinase, and mixtures thereof.

It is another object of the present invention to provide methods of treating or preventing a disease or condition in a mammal by modulating, for example activating, a kinase responsive to stress selected from the group consisting of Mst 1, Mst 2, 34 kDa Kinase, 50 kDa Kinase, and 130 kDa Kinase, and mixtures thereof.

It is another object of the present invention to provide compounds that are useful for modulating, for example activating, a kinase responsive to stress selected from the group consisting of Mst 1, Mst 2, 34 kDa Kinase, 50 kDa Kinase, and 130 kDa Kinase, and mixtures thereof.

It is another object of the present invention to provide pharmaceutical compositions comprising these compounds.

These and other objects will become readily apparent from the detailed description which follows.

SUMMARY OF THE INVENTION

The present invention relates to a method for identifying compounds which modulate a kinase responsive to stress selected from the group consisting of Mst 1, Mst 2, 34 kDa Kinase, 50 kDa Kinase, and 130 kDa Kinase, and combinations thereof, comprising:

a). contacting a putative activity-modifying compound with a cell culture selected from the group consisting of an osteoclastogenesis cell culture, purified osteoclasts, partially-purified osteoclasts, unpurified osteoclasts, purified pre-osteoclasts, partially-purified pre-osteoclasts, unpurified pre-osteoclasts, purified osteoclast-like cells, partially-purified osteoclast-like cells, unpurified osteoclasts-like cells, and mixtures thereof; and b). determining the kinase activity of said cell culture and comparing said kinase activity with a cell culture not contacted with said putative activity-modifying compound.

In further embodiments, the present invention relates to a method of activating or otherwise modulating in a mammalian cell a kinase responsive to stress selected from the group consisting of Mst 1, Mst 2, 34 kDa Kinase, 50 kDa Kinase, and 130 kDa Kinase, and combinations thereof, comprising contacting said cell with an activating or otherwise modulating amount of a compound identified according to the methods of the present invention.

In further embodiments, the present invention relates to a method of eliciting in a mammal an activating or otherwise modulating effect of a kinase responsive to stress selected from the group consisting of Mst 1, Mst 2, 34 kDa Kinase, 50 kDa Kinase, and 130 kDa Kinase, and combinations thereof, comprising administering to said mammal an activating amount of a compound identified according to the methods of the present invention.

In further embodiments, the present invention relates to a method of treating or preventing a disease or condition in a mammal that is mediated by a kinase responsive to stress selected from the group consisting of Mst 1, Mst 2, 34 k Da Kinase, 50 kDa Kinase, and 130 kDa Kinase, and combinations thereof, comprising administering to said mammal a pharmaceutically effective amount of a compound identified according to the methods of the present invention.

In further embodiments, the present invention relates to compounds useful for activating or otherwise modulating a kinase responsive to stress selected from the group consisting of Mst 1, Mst 2, 34 kDa Kinase, 50 kDa Kinase, and 130 kDa Kinase, and combinations thereof.

In further embodiments, the present invention relates to pharmaceutical compositions comprising these compounds.

BRIEF DESCRIPTION OF THE FIGURES

FIG. 4 shows activation of Mst 1, Mst 2, and 50 kDa Kinase by the echistatin RGD mimetics RGD I (10 nM) and RGD II (10 μM). Preosteoclasts from bone marrow and osteoblast (MB 1.8) cocultures were isolated as collagenase-insensitive, EDTA-sensitive cells (80–90% purity). Approximately 20 hr after purification, cells were treated with echistatin or the echistatin RGD mimetics. Timecourse (treatment and sampling at the indicated times) using echistatin to treat the cells shows maximal activity after 20 min treatment (left panel, FIG. 4A). The right panel.

DETAILED DESCRIPTION OF THE INVENTION

Figure 1A:
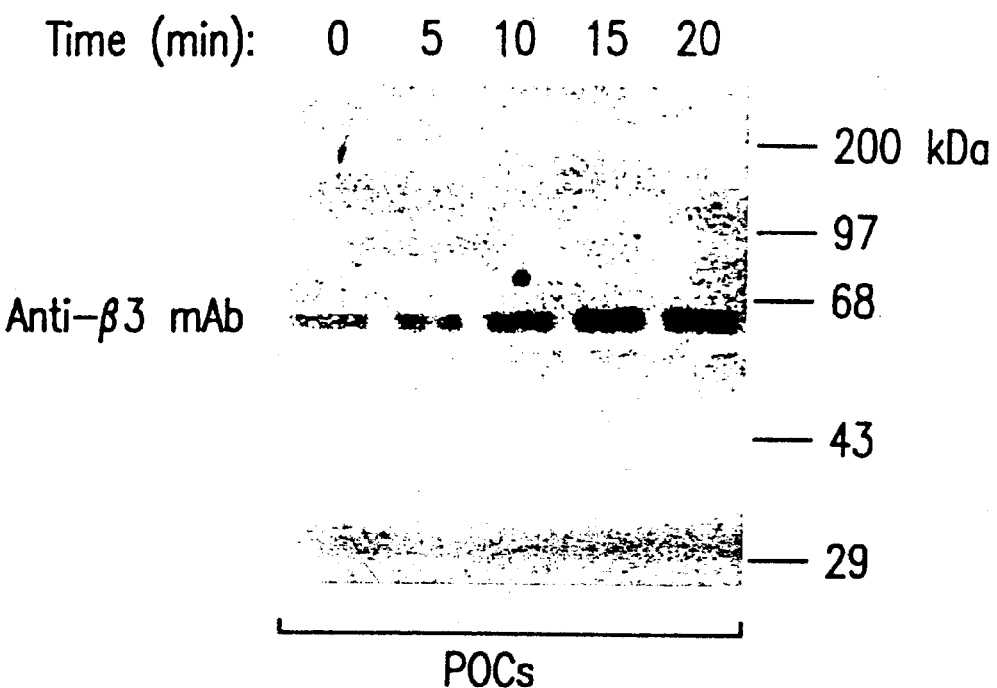
FIG. 1 shows the time course for activation of a kinase responsive to stress by anti β3 integrin monoclonal antibody (mAb) and by echistatin. Preosteoclasts (POCs) from bone marrow and osteoblast (MB 1.8) cocultures were isolated as collagenase-insensitive, EDTA-sensitive cells (80–90% purity). Approximately 20 hours after purification, the cells were treated with anti β3 integrin (mAb) (2 μg/ml) (top FIG. 1A) or echistatin (30 nM) (bottom FIG. 1B) for the indicated times. Kinase activities were determined using an in-gel kinase assay method employing myelin basic protein as a substrate. An approximately 60 kDa kinase doublet is strongly activated by both the anti β3 integrin mAb and by echistatin. A signal is also observed for a kinase of approximately 50 kDa, which is also activated by these treatments.
Figure 1B:
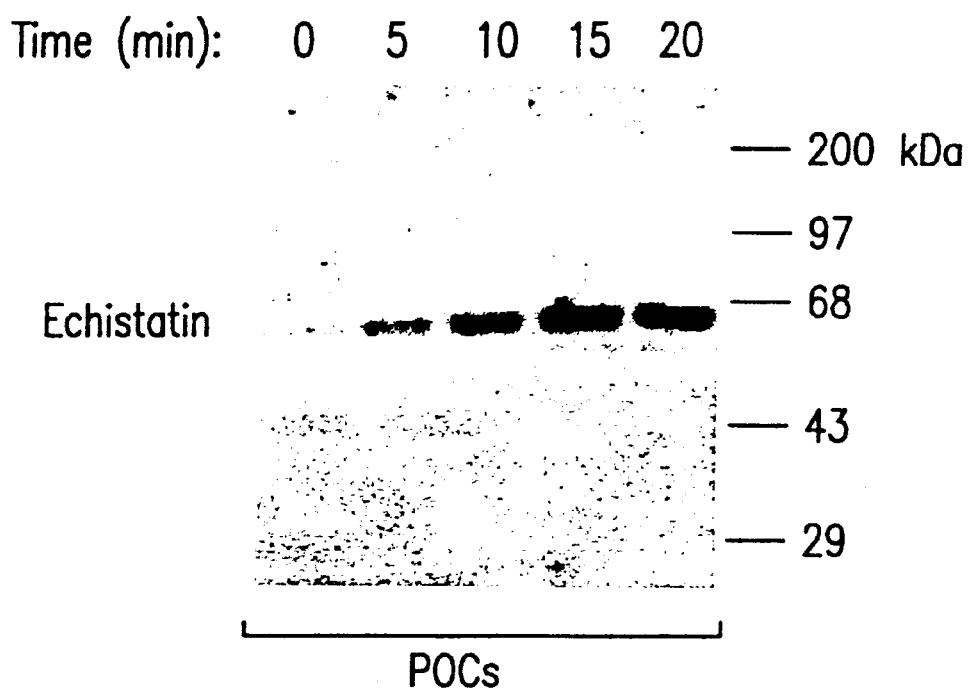
Figure 2A:
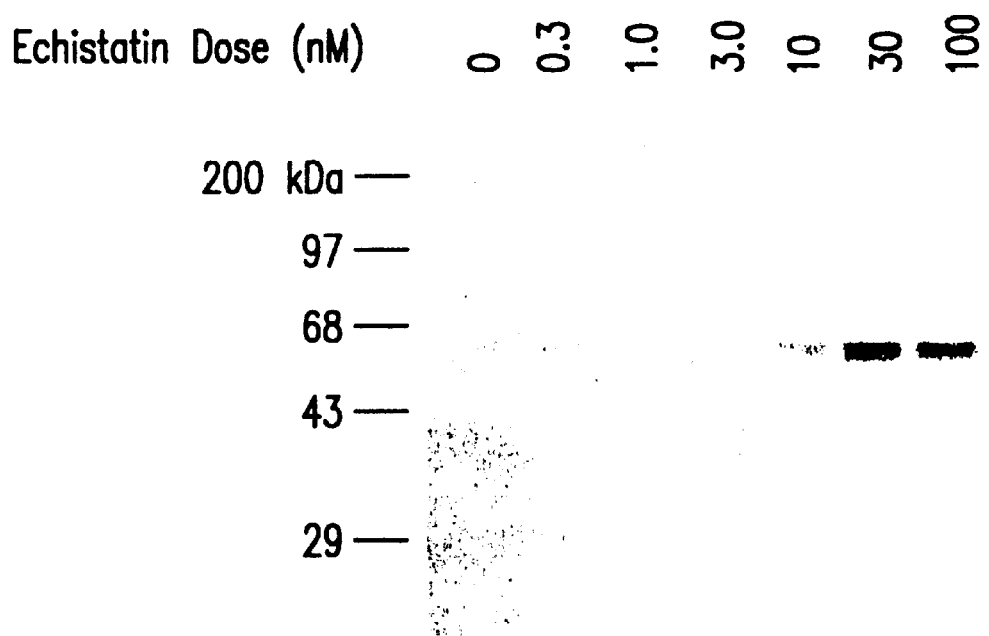
FIG. 2 shows a dose response for activation of 50–60 kDa kinases by echistatin. Preosteoclasts from bone marrow and osteoblast (MB 1.8) cocultures were isolated as collagenase-insensitive, EDTA-sensitive cells (80–90% purity). Approximately 20 hr after purification, cells were treated with varying concentrations of echistatin as indicated. Standard (i.e. overnight) film exposure (left panel FIG. 2A) shows activation of an approximately 60 kDa kinase doublet at concentrations ≧10 nM with maximal activities at about 30 nM. Extended (i.e. about 3–4 days) exposure (right panel FIG. 2B) shows activation of the approximately 50 kDa kinase at the 30 and 100 nM doses.
Figure 2B:
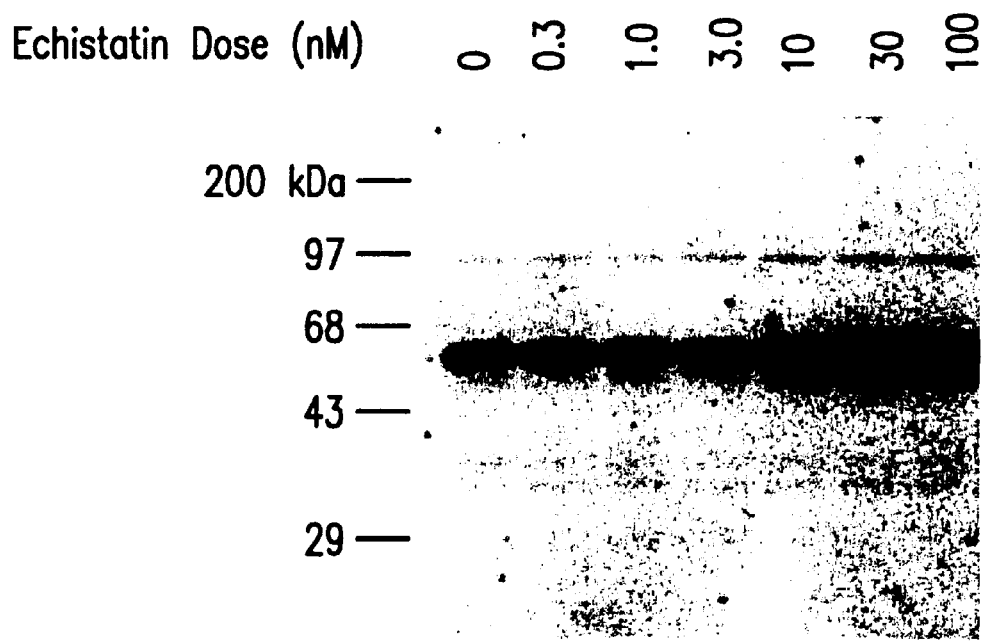
Figure 3:
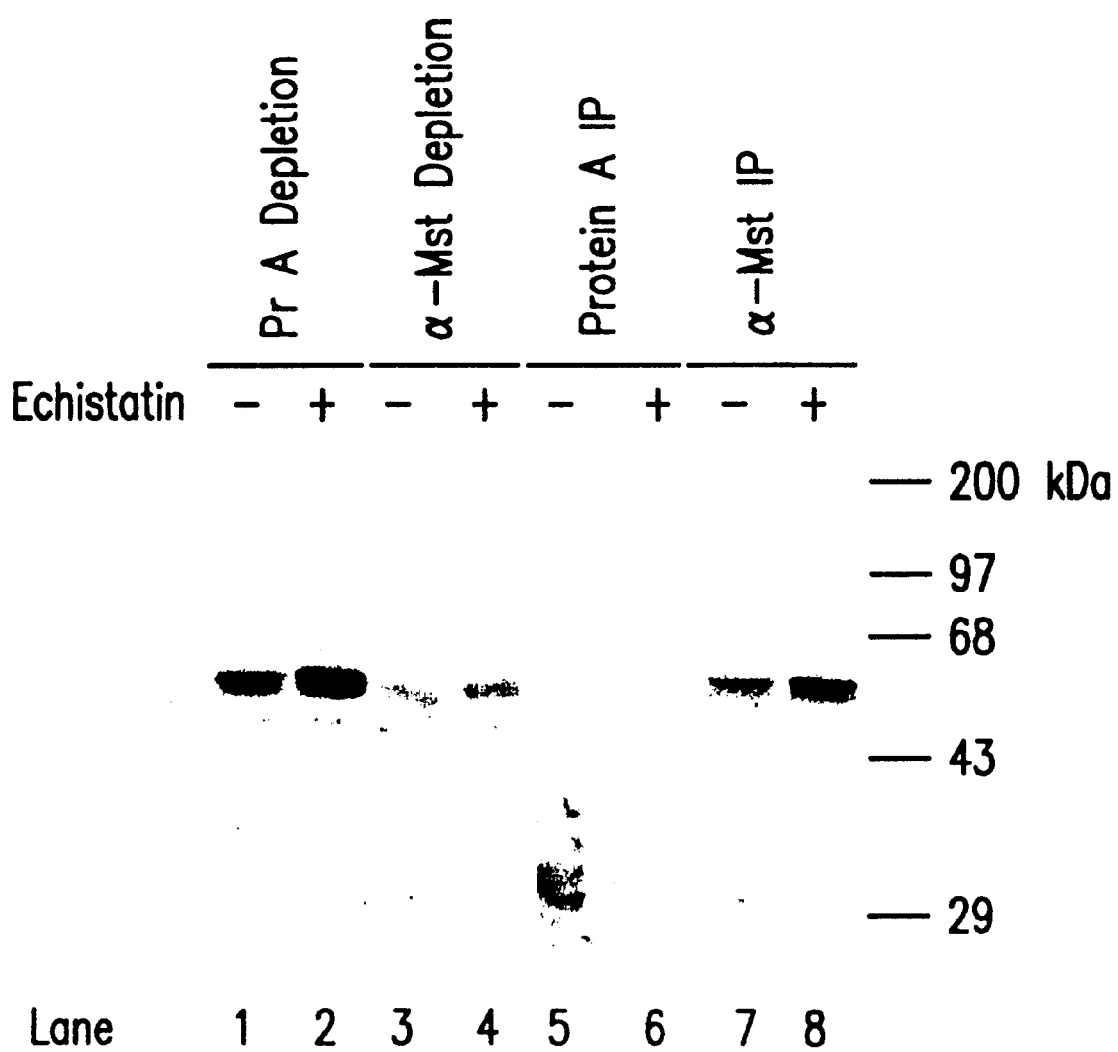
FIG. 3 shows the identification of the approximately 60 kDa kinase doublet as the two isoforms of the Mammalian Sterile 20-like (Mst) kinase. Preosteoclasts from bone marrow and osteoblast (MB 1.8) cocultures were isolated as collagenase-insensitive, EDTA-sensitive cells (80–90% purity). Approximately 20 hr after purification, cells were treated with echistatin as indicated (a plus "+" sign indicating treatment and a minus "−" sign indicating no treatment). Cell lysa-tes were exposed to treatment with a cocktail of commercially available anti Mst and Krs antibodies and Protein A-agarose beads to immunodeplete Mst from the samples. Control depletions without antibodies failed to diminish the 60 kDa kinase doublet (lanes 1 and 2) while treatment with the Mst/Krs antibody cocktail eliminated >90% of these activities (lanes 3 and 4). Corresponding activities associated with the Protein A-agarose beads showed that kinases were immunoprecipitated when the antibody cocktail was present in the mixture (lanes 7 and 8) and not when the antibody cocktail was absent (lanes 5 and 6).
Figures 4A, 4B:
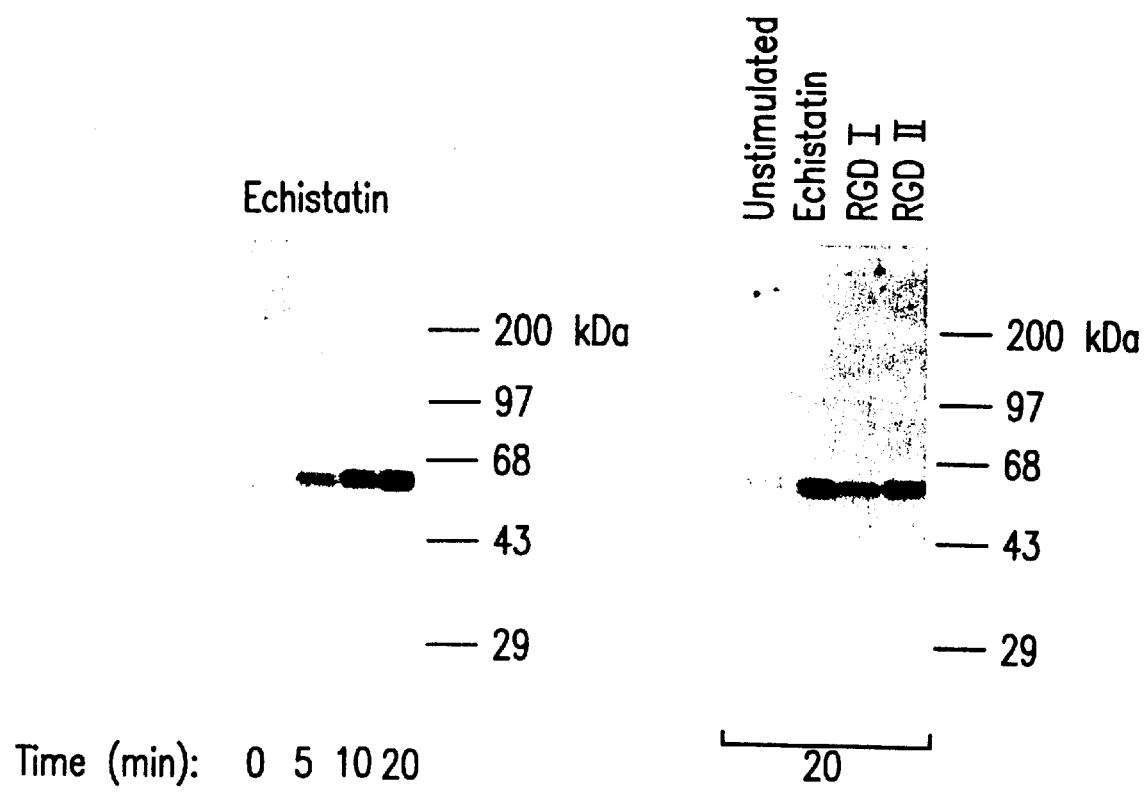
FIG. 4B shows that the echistatin RGD mimetics RGD I and RGD II are also effective in activating Mst 1, Mst 2, and 50 kDa kinase.
Figures 5D, 5E, 5F:
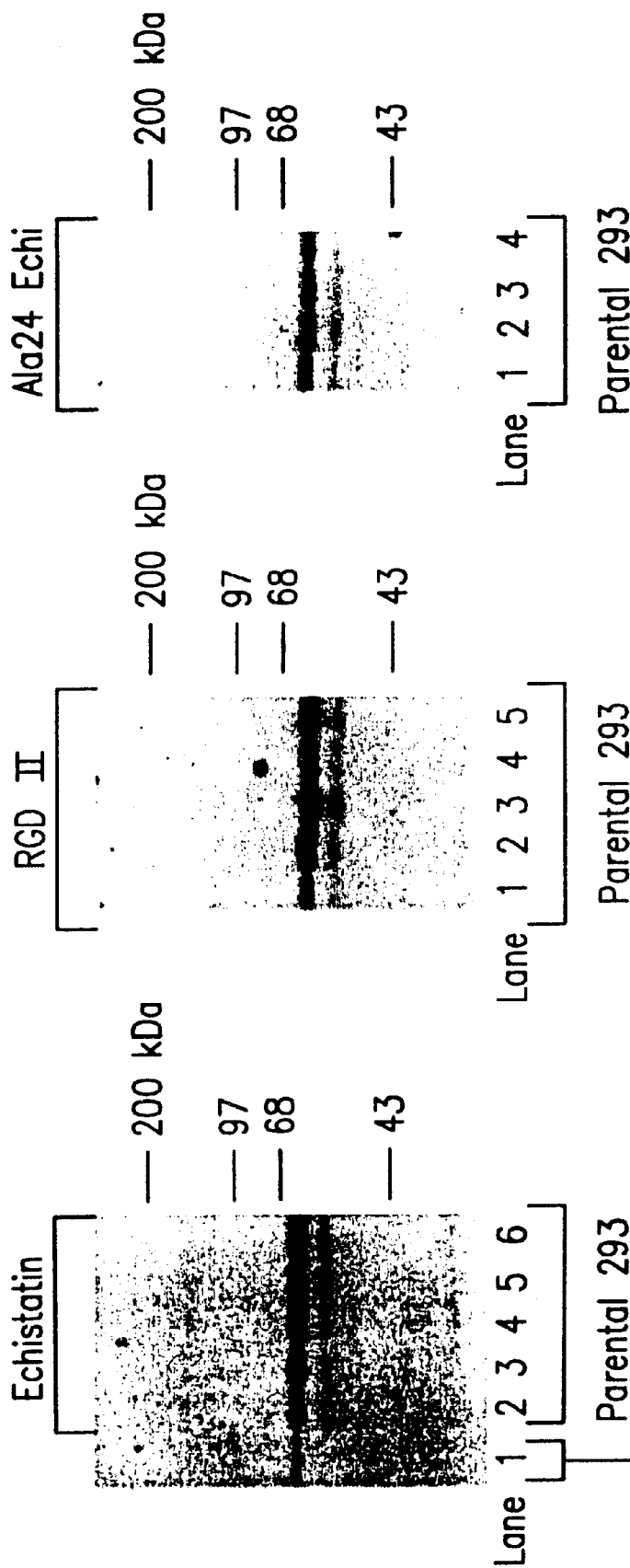
FIG. 5 shows that αvβ3 integrin expression in HEK 293 cells (human embryonic kidney 293 cells ATCC CRL 1573 sold by American Type Culture Collection) reduces basal kinase activities of Mst 1, Mst 2, and 50 kDa kinase. This effect is reversed by treatment with echistatin and RGD II, but not by a mutant echistatin, whose Arg-Gly-Asp sequence has been changed to Ala-Gly-Asp (Ala$^{24}$ Echistatin). HEK 293 transfectants expressing human αvβ3 integrin were treated with echistatin (30 nM, FIG. 5A) or RGD II (10 μM, FIG. 5B) for 0 min (lane 1), 10 min (lane 2) 20 min (lane 3), 30 min (lane 4) and 60 min (lane 5). These treatments resulted in an increase in Mst 1 (ca. 59 kDa), Mst 2 (ca. 60 kDa), and 50 kDa Kinase activities. Direct comparison αvβ3 integrin transfected HEK 293 cells (FIG. 5D, lane 1) to Parental HEK 293 cells (FIG. 5D, lane 2) shows that overexpression of αvβ3 integrin reduces basal activities of Mst 1, Mst 2, and 50 kDa Kinase. Maximal activities observed in FIGS. 5A and 5B, which are generated in response to treatments with echistatin or RGD II, are comparable to basal activities observed in the Parental HEK 293 control cells (FIG. 5D, lane 2, FIG. 5E, lane 1, and FIG. 5F, lane 1). Unlike in the transfected cells, treatment of Parental HEK 293 cells with echistatin (FIG. 5D) for 10 min (lane 3), 20 min (lane 4), 30 min (lane 5), or 60 min (lane 6) had no significant effect on activities of Mst 1, Mst 2, and 50 kDa Kinase. Similar results were obtained when RGD II was used instead of echistatin (FIG. 5E) for 10 min (lane 2), 20 min (lane 3), 30 min (lane 4) and 60 min (lane 5). Neither transfected HEK 293 cells (FIG. 5C) nor Parental HEK 293 cells (FIG. 5F) responded to Ala$^{24}$ echistatin (30 nM) for 0 min (lane 1), 10 min (lane 2 ), 30 min (lane 3 ), and 60 min (lane 4 ).
Figure 6:
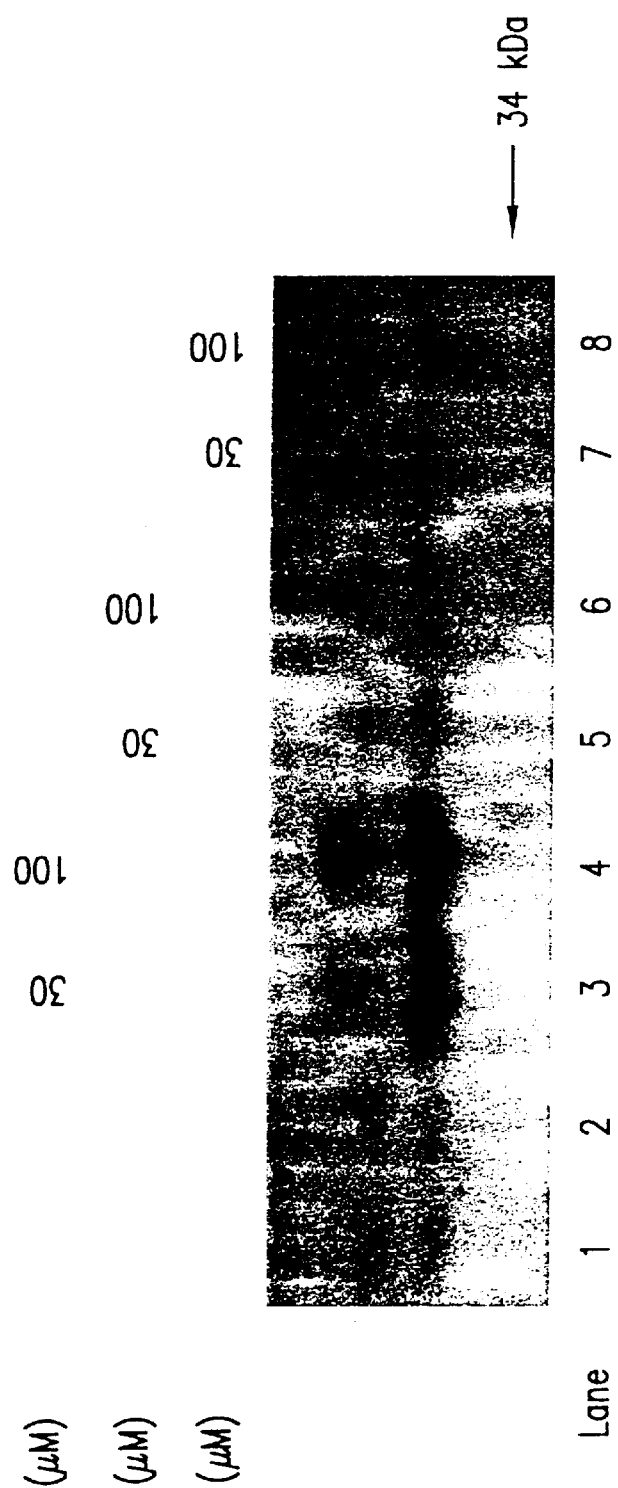
FIG. 6 shows the preferential response of 34 kDa Kinase to alendronate monosodium trihydrate. Osteoclast like cells were treated with alendronate monosodium trihydrate, etidronate disodium, or tiludronate disodium at concentrations of 30 μM and 100 μM for about 17 hours. Kinase activities were analyzed using the in-gel kinase assays. Autoradiographs were developed after film exposure for several days. These data show the activation of a 34 kDa Kinase by alendronate at either 30 μM (lane 3 ) or 100 μM (lane 4 ). Equivalent doses of etidronate disodium (lanes 5 and 6) or tiludronate disodium (lanes 7 and 8) failed to activate this kinase and were similar to no treatment controls (lanes 1 and 2).
Figure 7:
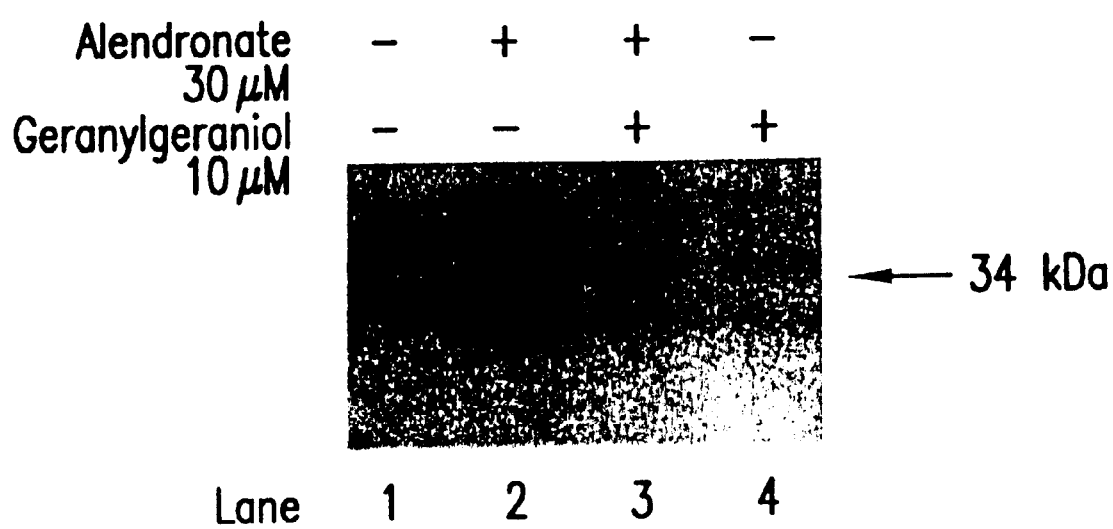
FIG. 7 shows the effect of 10 μM geranyl geraniol on the activation of osteoclast like cells with 30 μM alendronate monosodium trihydrate. Lane 1 shows a no treatment control. Lane 2 shows the activation of a 34 kDa Kinase by alendronate. Lane 3 shows that geranyl geraniol negates this activation. Lane 4 is a treatment control with only geranyl geraniol.
Figure 8:
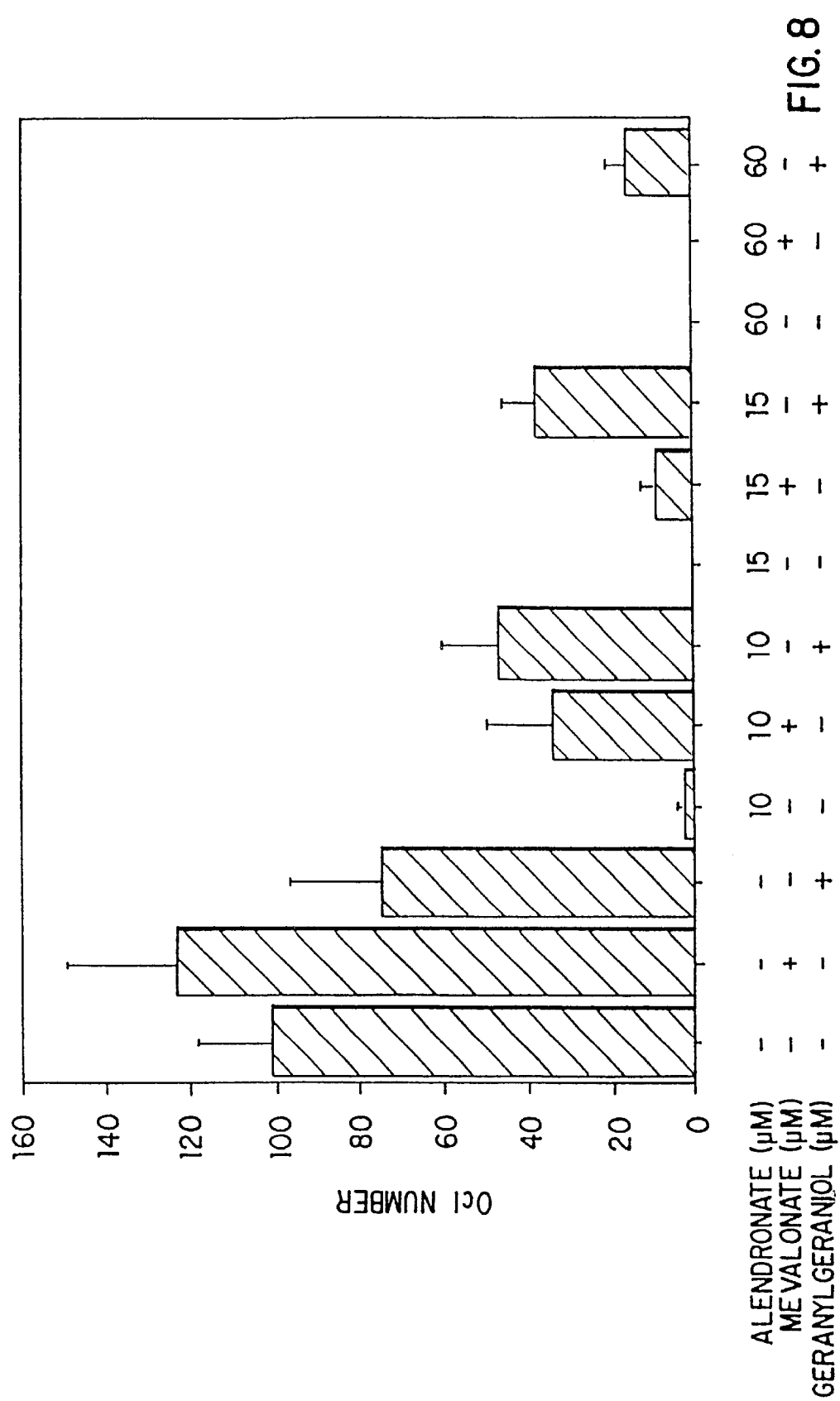
FIG. 8 shows the effect of 10, 15, and 60 μM alendronate monosodium trihydrate, 10 μM geranylgeraniol, 1 mM mevalonate, the combination of 10, 15, and 60 μM alendronate monosodium trihydrate and 10 μM geranylgeraniol, and the combination of 10, 15, and 60 μM alendronate monosodium trihydrate and 1 mM mevalonate on osteoclast like cells in terms of the formation of cells larger than 300 μm (as measured in one dimesion). The compounds were dosed both 5 and 6 days after establishing the culture, and the formation of 300 μm cells were counted using an inverted microscope with a 10X objective and quantitated versus a no treatment control.
Figure 9:
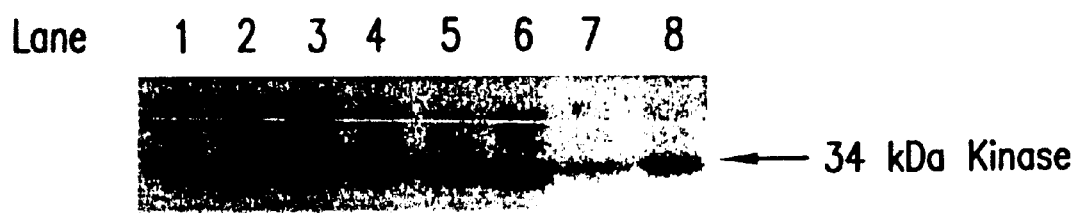
FIG. 9 shows the preferential response of 34 kDa Kinase to alendronate monosodium trihydrate and the inability of alendronate monosodium trihydrate to activate the 34 kDa Kinase when used to treat osteoclasts in the presence of the caspase inhibitor Z—Val—Ala—Asp(OMe)—CH$_2$F (hereafter Z—VAD—FMK). Osteoclast-like cells were treated with alendronate monosodium trihydrate at concentrations of 10 μM and 30 μM for about 17 hours. Kinase activities were analyzed using in-gel kinase assays. Autoradiographs were developed after film exposure for several days. These data show the activation of a 34 kDa Kinase by alendronate at either 10 μM (lane 2 ) or 30 μM (lane 3 ). Alendronate does not activate the 34 kDa Kinase when coincubated in the presence of Z—VAD—FMK (lane 8 ). Higher doses of etidronate disodium, i.e. 100 μM (lane 4 ) and 300 μM (lane 5 ), or tiludronate disodium, i.e. 100 μM (lane 6 ) and 300 μM (lane 7 ), failed to activate this kinase and were similar to no treatment control (lane 1 ). See J. D. Graves et al., "Caspase-mediated activation and induction of apoptosis by the mammalian Ste2-like kinase Mst1", *The EMBO Journal*, vol. 17, no. 8, pp. 2224–2234 (1998), which is incorporated by reference herein in its entirety.
Figure 10:
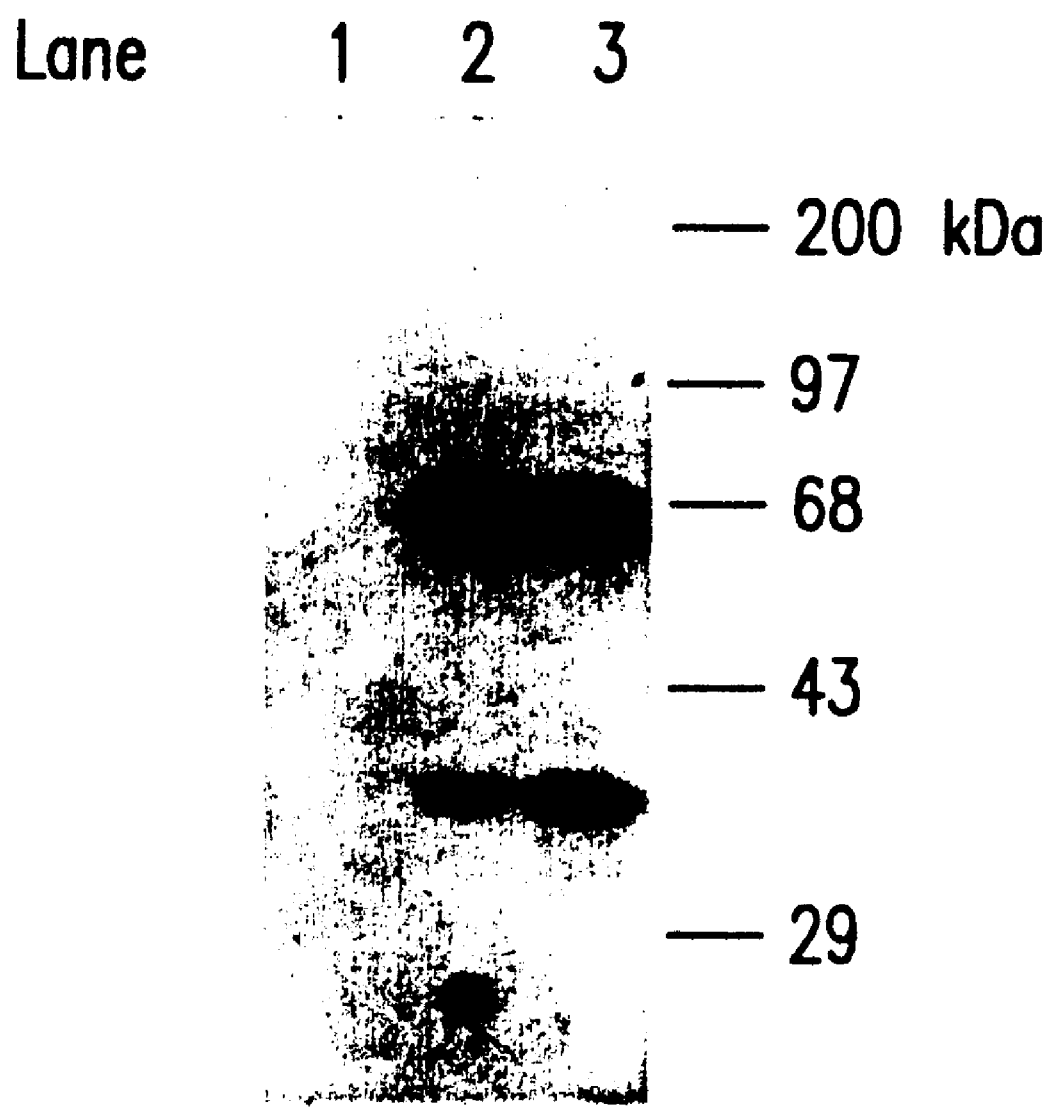
FIG. 10 shows identification of 34 kDa kinase activated by alendronate monosodium trihydrate (30 μM) as an amino-terminal cleavage product of Mst. Osteoclast-like cells were isolated and treated with alendronate monosodium trihydrate. Cell lysates were exposed to treatment with a cocktail of commercially available anti-Mst and anti-Krs antibodies that recognize the amino-terminus of Mst kinase and Protein A-agarose beads to immunoprecipitate Mst from the samples. These were analyzed using the in-gel kinase assay. These data demonstrate that the anti-Mst and anti-Krs antibody cocktail immunoprecipitates the full length 59 and 60 kDa Mst Kinases as well as the 34 kDa Mst Kinase cleavage product in untreated osteoclasts (lane 2 ) and alendronate-treated osteoclasts (lane 3 ). No kinase activities are immunoprecipitated in the absence of anti-Mst and anti-Krs antibodies (lane 1 ). These data also demonstrate that the 34 kDa Kinase immunoprecipitated by the anti-Mst and anti-Krs antibody cocktail is activated by alendronate monosodium trihydrate (lane 3 ).

Several methods of inhibiting oscteoclast activity in mammals, and in particular for treating osteoporosis, are known. These methods include treatment with bisphosphonates [for example alendronate (especially alendronate monosodium trihydrate), cimadronate, clodronate, tiludronate, etidronate, ibandronate, neridronate, olpandronate, risedronate, piridronate, pamidronate, zolendronate, pharmaceutically acceptable salts thereof, and mixtures thereof], hormones such as estrogen, or certain peptides such as calcitonin.

In the present invention, an approach has been employed using in-gel kinase assays to identify kinases whose activities change in the osteoclast system during treatment with these and other agents. Identification of the two isoforms of the Mammalian Sterile 20-like (Mst) kinases, Mst 1 and Mst 2, and of the 34 kDa Kinase, the 50 kDa Kinase, and the 130 kDa Kinase, provided the first readout of signal transduction and stress response pathways that respond to these drugs. This initial work led to the unexpected discovery that it would be possible to identify compounds that are useful for activating these kinases and that such activator compounds would be useful for treating or preventing disease states mediated by such kinases.

In the present invention, the kinases that are activated, i.e. Mst 1, Mst 2, the 34 kDa Kinase, the 50 kDa Kinase, and the 130 kDa Kinase are identified with in-gel kinase assays as in Example 2. Also, standard immunoprecipitation techniques have been employed in the further identification of Mst 1 and Mst 2. An aspect of this invention is an assay for the identification of compounds which modulate, preferably activate, these kinases. This comprises the steps of contacting a putative activity-modifying compound with an osteoclastogenesis cell culture, and determining the kinase activity of the cell culture by comparing its kinase activity with a control cell culture, i.e. a cell culture that had not been contacted with the activity-modifying compound. A wide variety of cell cultures known to one of ordinary skill in the art can be employed. Preferably, the cultures are selected from the group consisting of an osteoclastogenesis cell culture, purified osteoclasts, partially-purified osteoclasts, unpurified osteoclasts, purified pre-osteoclasts, partially-purified pre-osteoclasts, unpurified pre-osteoclasts, purified osteoclast-like cells, partially-purified osteoclast-like cells, unpurified osteoclasts-like cells, and mixtures thereof. A preferred cell culture is one containing mammalian bone marrow cells. For example, purified, i.e. about 80–90% pre-osteoclast cells generated by co-culturing mouse bone marrow cells and mouse calvaria osteoblasts can be used. Alternatively, similar cells derived from avian bone sources can be used.

A wide variety of techniques known to one of ordinary skill in the art can be employed for measruing kinase activity. A preferred methodology involves an in-gel kinase assay in which the samples are subjected to electrophoresis in the presence of an appropriate immobolized kinase substrate and then measured for kinase activity against that substrate. This method provides a convenient technique for assaying multiple samples and rapidly quantitating the activity of the eletrophoresed kinases.

Other techniques that can be used to quantitate kinase activity include, but are not limited to, immunoprecipitation, chromotagraphy, addition of selective inhibitors for retaining the activity of only the desired kinase, and use of selective substrates. In these assays, kinase activities are generaly assayed in-solution rather than in-gel.

Methods for Modulating a Kinase Responsive to Stress in a Mammalian Cell

The present invention also relates to a method for modulating, e.g. activating, a kinase responsive to stress in a mammalian cell, wherein said kinase responsive to stress selected from the group consisting of Mst 1, Mst 2, 34 kDa Kinase, 50 kDa Kinase, and 130 kDa Kinase, and combinations thereof. These methods comprise contacting said cell with an activating amount of a compound selected from the group consisting of an organic bisphosphonate, echistatin, anti β3 integrin monoclonal antibody, calcitonin, 3(S)-(2-(2-oxo-3(S)-[5,6,7,8-tetrahydro-[1,8]-naphthyridin-2-ylmethyl)-amino]-pyrrolidin-1-yl)-acetylamino)-4-quinolin-3-yl-butyric acid trihydrochloride, (2-[N-(3,4,5,6-tetrahydropyrimidin-2-yl)amino]ethyloxyphen-4-yl) carbonyl-2(S)-phenylsulfonamido-beta-alanine, and mixtures thereof.

Without being limited by theory, it is believed that as a subclass of the organic bisphosphonates, that the nitrogen containing bisphosphonates act by inhibiting protein prenylation, most critially geranylgeranylation. Nitrogen containing bisphosphonates such as alendronate, risedronate, and pamidronate induce activation of the 34 kDa Mst kinase. Clodronate, and to a lesser extent, etidronate (both non-nitrogen containing bisphosphonates) also induce the 34 kDa Mst kinase. It is found that the mevalonate pathway is inhibited with lovastatin, thus blocking the genesis of isoprenyl and cholesterol precursors. Treatment with lovastain for 17–24 hours increases the 34 kDa Mst 1 activity, indicating that a block in protein prenylation or cholesterol biosynthesis can cause Mst 1 cleavage. It is found that alendronate- and risedronate-induced Mst 1 cleavage is essentially completely blocked by geranylgeraniol, while farnesol and mevalonic acid lactone reduce cleavage by about 50%. Lovastatin effects are blocked by mevalonic acid or geranylgeraniol, but not by farnesol. Clodronate effects are not blocked by geranylgeraniol, suggesting that clodroante does not act by inhibiting protein prenylation. These findings suggest that Mst kinase is part of a stress responsive pathway activated in purified osteoclasts by nitrogen containing and non-nitrogen containing bisphosphonates. Geranylgeranylation appears to play a critical role in the mechanism of action of nitrogen containing bisphsophonates, but not in the mechanism of action of the non-nitrogen containing bisphosphonates. Mst 1 cleavage is mediated by caspases downstream of geranylgernaylated proteins, a group that includes small G-proteins that regulate apoptosis, the cytoskeleton, and vesicular trafficking. However, even though nitrogen containing bisphosphonates may act via a different mechanism of action, these findings are in no way intended to limit the present invention to such bisphosphonates.

Organic Bisphosphonates

The methods and compositions of the present invention, can comprise a bisphosphonate active. The bisphosphonates of the present invention correspond to the chemical formula

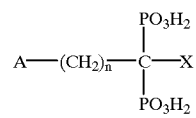

wherein n is an integer from 0 to 7 and wherein A and X are independently selected from the group consisting of H, OH, halogen, $NH_2$, SH, phenyl, C1-C30 alkyl, C3-C30 branched or cycloalkyl, C1-C30 substituted alkyl, C1-C10 alkyl substituted $NH_2$, C3-C10 branched or cycloalkyl substituted $NH_2$, C1-C10 dialkyl substituted $NH_2$, C3-C10 branched or cycloalkyl disubstituted $NH_2$, C1-C10 alkoxy, C1-C10 alkyl substituted thio, thiophenyl, halophenylthio, C1-C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3-C10 ring.

In the foregoing chemical formula, the alkyl groups can be straight, branched, or cyclic, provided that sufficient atoms are selected for the chemical formula. The C1-C30 substituted alkyl can include a wide variety of substituents, nonlimiting examples which include those selected from the group consisting of phenyl, pyridyl, furanyl, pyrrolidinyl, imidazonyl, $NH_2$, C1-C10 alkyl or dialkyl substituted $NH_2$, OH, SH, and C1-C10 alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

A non-limiting class of structures useful in the instant invention are those in which A is selected from the group consisting of H, OH, and halogen, X is selected from the group consisting of C1-C30 alkyl, C1-C30 substituted alkyl, halogen, and C1-C10 alkyl or phenyl substituted thio, and n is 0.

A non-limiting subclass of structures useful in the instant invention are those in which A is selected from the group consisting of H, OH, and Cl, X is selected from the group consisting of C1-C30 alkyl, C1-C30 substituted alkyl, Cl, and chlorophenylthio, and n is 0.

A non-limiting example of the subclass of structures useful in the instant invention is when A is OH and X is a 3-aminopropyl moiety, and n is 0, so that the resulting compound is a 4-amino-1,-hydroxybutylidene-1,1-bisphosphonate, i.e. alendronate.

Pharmaceutically acceptable salts and derivatives of the bisphosphonates are also useful herein. Nonlimiting examples of salts include those selected from the group consisting alkali metal, alkaline metal, ammonium, and mono-, di, tri-, or tetra-C1-C30-alkyl-substituted ammonium. Preferred salts are those selected from the group consisting of sodium, potassium, calcium, magnesium, and ammonium salts. Nonlimiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those or ordinary skill in the art, reference to a specific weight or percentage of a bisphosphonate compound in the present invention is on an acid active weight basis, unless indicated otherwise herein. For example, the phrase "about 5 mg of a bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid. For other bisphosphonates, the amount of bisphosphonate is calculated based on the corresponding bisphosphonic acid.

Nonlimiting examples of bisphosphonates useful herein include the following:

Alendronic acid, 4-amino-1-hydroxybutylidene-1,1-bisphosphonic acid.

Alendronate (also known as alendronate sodium or alendronate monosodium trihydrate), 4-amino-1-hydroxybutylidene-1,1-bisphosphonic acid monosodium trihydrate.

Alendronic acid and alendronate are described in U.S. Pat. Nos. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-($1^H$-imidazol-1-yl)ethylidene-1,1-bisphosphonic acid (zolendronate).

A non-limiting class of bisphosphonates useful in the instant invention are selected from the group consisting of alendronate, cimadronate, clodronate, tiludronate, etidronate, ibandronate, neridronate, olpandronate, risedronate, piridronate, pamidronate, zolendronate, pharmaceutically acceptable salts thereof, and mixtures thereof.

A non-limiting subclass of the above-mentioned class in the instant case is selected from the group consisting of alendronate, pharmaceutically acceptable salts thereof, and mixtures thereof.

A non-limiting example of the subclass is alendronate monosodium trihydrate.

The following Examples are presented to better illustrate the invention.

EXAMPLE 1

Preparation of Preosteoclasts and Osteoclast-like Cells From Bone Marrow/Calivaria Cell Cocultures The following procedure is a modification of Wesolowski et al. (1995, *Exp. Cell Res.* 219: 679–686), which is incorporated by reference herein in its entirety. Cocultures are made by adding marrow cells from 6-week old mouse tibia and femur onto a monolayer of MB 1.8 mouse calvaria osteoblasts that are preseeded into culture dishes in α-MEM (minimal essential medium) containing fetal calf serum (10%) and 1,25 Dihydroxy Vitamin D3 (10 nM). Cocultures are maintained, with media changes every 48 hours, for a period of 6 days. Non-osteoclastic cells are removed by treatment of cocultures with Collagenase I (1 mg/ml in Phosphate Buffered Saline [PBS]). Collagenase-sensitive cells are removed by washing with PBS. Preosteoclasts are lifted from the dish using EDTA (0.2 g/L in PBS) and transferred into culture dishes and maintained in α-MEM containing fetal calf serum (10%), 1,25 Dihydroxy Vitamin D3 (10 nM), and m-Colony Stimulating Factor (5 ng/ml). Osteoclast-like cells (collagenase-insensitive, EDTA-insensitive cells) that remain attached to the original coculture dishes are maintained in α-MEM containing fetal calf serum (10%), 1,25 Dihydroxy Vitamin D3 (10 nM), and m-Colony Stimulating Factor (5 ng/ml).

EXAMPLE 2

Method to Examine Activity Change in Mst1, Mst2, and 50 kDa Kinase in Response to Treatment of Osteoclast-Like Cells with Inhibitors Preosteoclasts are generated and purified as described in Example 1. After cells have recovered 1–2 hr at 37° C., cells are treated with echistatin (typically 30 nM, although a range of 1 pM to 1 μM can be used). Untreated cells are included in the analyses and act as a negative control for kinase activities. Cells are then harvested and lysed in a HEPES (N-(2-hydroxyethyl)piperazine-N'-(2-ethansulfonic acid) or Tris buffer containing the following: β-glycerophosphate (50 mM); $Na_3VO_4$ (1 mM); NaF (1 mM); Microcystin LR (1 μM); leupeptin (10 μg/ml); aprotinin (10 μg/ml); phenylmethyl sulfonylfluoride (1 mM). Protein concentrations are determined for each lysate and 5–20 μg are loaded into each lane of a SDS-PAGE (sodium dodecyl sulfate-polyacrylamide gel electrophoresis) gel containing Myelin Basic Protein, or another kinase substrate, which has been polymerized into the gel at a concentration between 50–400 μg/ml. Molecular weight standards are also loaded into one or more lanes of the gels. In-gel kinase assays are run according to a standard procedure based on Kameshita and Fujisawa, 1989 (Anal. Biochem. 183:139–143) and of Gotoh et al., 1990 (Eur. J. Biochem. 193: 661–669), both references being incorporated by reference herein in their entirety. The proteins are electrophoresed in the above gels. The gels are then successively soaked in 50 mM HEPES, pH 7.6; 5 mM 2-mercaptoethanol and each of the following (for each wash): (a) 20% isopropanol; (b) no additions; (c) urea (6 M); (d) Urea (3 M); (e) Urea (0.75 M); and Tween 20 (0.05% vol:vol). Kinase reactions are then run by first soaking the gels in 20 mM HEPES, pH 7.6; 20 mM $MgCl_2$; 2 mM DTT and then in the same buffer containing 0.02 M ATP (non-radioactive) with ca. 1000 cpm/pmol $^{32}P$-γ-ATP. The gels are then washed six times with 5% trichloroacetic acid and 1% pyrophosphate. The gels are then stained with Coomassie brilliant blue dye (0.125%) in 50% methanol, 10% acetic acid; destained with 30% methanol, 10% acetic acid; soaked in 2% glycerol; and dried using a gel dryer. The gels are then exposed to autoradiography film for times ranging from several hours to weeks. The bands observed in the autoradipgraphs representing the gels reflect kinase activities. Mst 1 (apparent molecular weight about 59 kDa), Mst 2 (apparent molecular weight about 60 kDa), and 50 kDa kinase are observed and identified by their migration as compared to the migration of molecular weight standards. The band intensities on the autoradiography film are quantitated by densitometry and comparisons between bands from untreated controls and bands from echistatin-treated cells provide the basis for the analyses.

A similar approach is used for alendronate, calcitonin, anti β3 integrin monoclonal antibody, RGD I, and RGD II.

A similar approach is also used to assay for the 34 kDa Kinase and the 130 kDa Kinase.

EXAMPLE 3

General Method for Identifying Compounds which Activate Mst 1, Mst 2, 34 kDa Kinase, 50 kDa Kinase, and 130 kDa Kinase in Osteoclast-Like Cells Osteoclast-like cells are generated as described in Example 1. The compound or compounds to be evaluated are added at the desired concentration to the osteoclast-like cells for any of various times (1 minute to several hours). Cell lysates are made using standard techniques and in-gel kinase assays are performed as described in Example 2. Compounds that inhibit osteoclast function are identified by their ability to stimulate Mst 1, Mst 2, 34 kDa Kinase, 50 kDa Kinase and/or 130 kDa Kinase activities.

What is claimed is:

1. A method for identifying compounds which are useful for treating abnormal bone resorption or angiogenesis comprising:
   (a). contacting a putative activity-modifying compound with a cell culture;
   (b). determining the kinase activity of said cell culture and comparing said kinase activity with a cell culture not contacted with said putative activity-modifying compound; and
   (c). identifying a compound which activates a kinase response to stress thereby identifying a compound useful for treating abnormal bone resorption or angiogenesis.

2. A method according to claim 1 wherein said kinase responsive to stress is selected from the group consisting of Mst 1, Mst 2, 34 kDa kinase which regulates osteoclast function and is an amino terminal clevage product of Mst, 50 kDa kinase which regulates osteoclast function and is activated by echistatin or an organic bisphosphonate and 130 kDa kinase which regulates osteoclast function and is activated by echistatin or an organic biphosphonate, and combinations thereof.

3. A method according to claim 2 wherein said cell culture is selected from the group consisting of an osteoclastogenesis cell culture, purified osteoclasts, partially-purified osteoclasts, unpurified osteoclasts, purified pre-osteoclasts, partially-purified pre-osteoclasts, unpurified pre-osteoclasts, purified osteoclast-like cells, partially-purified osteoclast-like cells, unpurified osteoclasts-like cells, and mixtures thereof.

4. A method according to claim 3 wherein said kinase activity is determined using an in-gel kinase assay.

* * * * *